United States Patent
Kunihiro et al.

(10) Patent No.: US 10,157,459 B2
(45) Date of Patent: Dec. 18, 2018

(54) CELL EVALUATION APPARATUS AND METHOD TO SEARCH FOR AN AREA TO BE OBSERVED IN CARDIOMYOCYTES

(71) Applicant: SONY CORPORATION, Tokyo (JP)

(72) Inventors: Takeshi Kunihiro, Kanagawa (JP); Tomohiro Hayakawa, Saitama (JP); Eriko Matsui, Tokyo (JP); Seiji Kobayashi, Tokyo (JP)

(73) Assignee: SONY CORPORATION, Tokyo (JP)

( * ) Notice: Subject to any disclaimer, the term of this patent is extended or adjusted under 35 U.S.C. 154(b) by 92 days.

(21) Appl. No.: 14/904,861

(22) PCT Filed: Jul. 10, 2014

(86) PCT No.: PCT/JP2014/068377
§ 371 (c)(1),
(2) Date: Jan. 13, 2016

(87) PCT Pub. No.: WO2015/008682
PCT Pub. Date: Jan. 22, 2015

(65) Prior Publication Data
US 2016/0163044 A1     Jun. 9, 2016

(30) Foreign Application Priority Data

Jul. 19, 2013 (JP) ................................. 2013-150435

(51) Int. Cl.
*G06K 9/00* (2006.01)
*G06T 7/00* (2017.01)
(Continued)

(52) U.S. Cl.
CPC .......... *G06T 7/0012* (2013.01); *C12M 41/46* (2013.01); *C12N 5/0657* (2013.01); *G01N 15/10* (2013.01);
(Continued)

(58) Field of Classification Search
CPC ......... G06T 7/0012; G06T 7/32; G06T 7/246; G06T 7/0016; G06T 2207/30024;
(Continued)

(56) References Cited

U.S. PATENT DOCUMENTS

2013/0070971 A1 *  3/2013  Kunihiro ............... G06T 7/0016
                                                    382/107

FOREIGN PATENT DOCUMENTS

JP      2004-340738       12/2001
JP      2004-340738 A     12/2004
(Continued)

OTHER PUBLICATIONS

Hayakawa, Tomohiro, et al. "Noninvasive evaluation of contractile behavior of cardiomyocyte monolayers based on motion vector analysis." Tissue Engineering Part C: Methods 18.1 (2011): 21-32.*

(Continued)

*Primary Examiner* — Andrew Moyer
(74) *Attorney, Agent, or Firm* — Chip Law Group

(57) ABSTRACT

The present technology relates to a cell evaluation apparatus and method, and a program that are capable of easily searching for an area to be observed within cardiomyocytes without requiring special preparation.

The cell evaluation apparatus includes: a motion detecting section configured to detect motion of cultured cardiomyocytes for each of partial areas of a plurality of observation fields on the cultured cardiomyocytes; a motion amount calculating section configured to calculate a motion amount of the detected motion; a pulsation information calculating section configured to calculate pulsation information on a characteristic amount of pulsations of the cultured cardiomyocytes on the basis of the calculated motion amount; an evaluation value calculating section configured to calculate an evaluation value corresponding to the plurality of obser- (Continued)

vation fields, calculated on the basis of the pulsation information; and a field determining section configured to determine an observation field to be observed on the cultured cardiomyocytes, on the basis of the evaluation value.

10 Claims, 18 Drawing Sheets

(51) Int. Cl.
*G01N 33/50* (2006.01)
*G01N 15/10* (2006.01)
*C12M 1/34* (2006.01)
*C12N 5/077* (2010.01)
*G01N 33/483* (2006.01)
*G06T 7/32* (2017.01)
*G06T 7/246* (2017.01)

(52) U.S. Cl.
CPC ..... *G01N 33/4833* (2013.01); *G01N 33/5005* (2013.01); *G06K 9/00134* (2013.01); *G06T 7/0016* (2013.01); *G06T 7/246* (2017.01); *G06T 7/32* (2017.01); *G01N 2015/1006* (2013.01); *G06T 2207/20021* (2013.01); *G06T 2207/30024* (2013.01); *G06T 2207/30048* (2013.01)

(58) Field of Classification Search
CPC ........... G06T 2207/20021; G06T 2207/30048; C12M 41/46; G01N 33/4833; G01N 15/10; G01N 33/5005; C12N 5/0657; G06K 9/00134

USPC .................................................. 382/133, 134
See application file for complete search history.

(56) References Cited

FOREIGN PATENT DOCUMENTS

| JP | 2012-105631 | | 6/2012 |
|---|---|---|---|
| JP | 2012-105631 | A | 8/2012 |
| JP | 2012-254042 | | 12/2012 |
| JP | 2012-254042 | A | 12/2012 |
| JP | 2014-075999 | | 5/2014 |
| JP | 2014-075999 | A | 5/2014 |
| JP | 2014-076000 | | 5/2014 |
| JP | 2014-076000 | A | 5/2014 |
| WO | 2011-122200 | | 10/2011 |
| WO | 2011/122200 | A | 10/2011 |
| WO | 2012-118049 | | 9/2012 |
| WO | 2012/118049 | A | 9/2012 |
| WO | 2013-165301 | | 11/2013 |
| WO | 2013/165301 | A | 11/2013 |

OTHER PUBLICATIONS

Tomohiro Hayakawa et al., "Noninvasive Evaluation of Contractile Behavior of Cardiomyocyte Monolayers Based on Motion Vector Analysis", vol. 18, Nov. 1, 2012.
Tomohiro Hayakawa et al, "Noninvasive Evaluation of Contractile Behaviour of Cardiomyocyte Monolayers Based on Motion Vector Analysis", Jan. 4, 2012, pp. 15, Tissue Engineering Part C: Methods, vol. 18, Issue 1.

* cited by examiner

CELL EVALUATION APPARATUS AND METHOD TO SEARCH FOR AN AREA TO BE OBSERVED IN CARDIOMYOCYTES

TECHNICAL FIELD

The present technology relates to a cell evaluation apparatus and method, and a program, and more particularly, to a cell evaluation apparatus and method and a program that are capable of easily searching for an area to be observed in cardiomyocytes without requiring special preparation.

BACKGROUND ART

In recent years, in the study of cellular processes and the like, a technology called calcium (Ca) imaging has been used, in which cells and the like are dyed using a pigment (calcium fluorescent indicator), the pigment being bonded to calcium ions to emit fluorescence, and are observed as image information.

Further, an evaluation using a multi-electrode array (MEA) is also performed. In the evaluation using the MEA, a change in extracellular membrane potential is detected by electrodes disposed on the bottom of a culture dish.

Further, an image processing technology by which pulsations can be observed easily and non-invasively is also proposed (see, for example, Patent Document 1).

Patent Document 1: WO 2012/118049

SUMMARY OF INVENTION

Problem to be Solved by the Invention

In the related art, however, a field of view used in experiments and the like have been determined qualitatively through verification of pulsations in cardiomyocytes by human visual contact. For that reason, for example, it has been difficult to search for an area of cardiomyocytes to be compared before and after medication.

For example, there have been techniques to search for a target cell by using shape information or luminance information of cardiomyocytes and simple motion information on a difference between frames and the like. However, information on the number of pulsations, a contraction speed, and the like have not been taken into consideration, and thus this makes it difficult to know whether cardiomyocytes are actively pulsating or not, for example.

The present technology is disclosed in view of the circumstances as described above and aims at enabling easily searching for an area to be observed in cardiomyocytes without requiring special preparation.

Means for Solving the Problem

According to a first aspect of the present technology, there is provided a cell evaluation apparatus including: a motion detecting section configured to detect motion of cultured cardiomyocytes for each of partial areas of a plurality of observation fields on the cultured cardiomyocytes; a motion amount calculating section configured to calculate a motion amount of the detected motion; a pulsation information calculating section configured to calculate pulsation information on a characteristic amount of pulsations of the cultured cardiomyocytes on the basis of the calculated motion amount; an evaluation value calculating section configured to calculate an evaluation value corresponding to the plurality of observation fields, calculated on the basis of the pulsation information; and a field determining section configured to determine an observation field to be observed on the cultured cardiomyocytes, on the basis of the evaluation value.

The pulsation information may be a pulsation area of the cultured cardiomyocytes within the observation field.

The motion detecting section may detect the motion for each of the partial areas in each of frames of a moving image of the observation area, and the pulsation information calculating section may generate, on the basis of the motion amount for each of the partial areas of the plurality of frames of the moving image, wave shape information representing the pulsations of the cultured cardiomyocytes of each of the partial areas.

The pulsation information may be a number of pulsations of the cultured cardiomyocytes within the observation field within a unit time, calculated on the basis of the wave shape information.

The pulsation information may be a contraction time or a relaxation time of the pulsations of the cultured cardiomyocytes within the observation field, calculated on the basis of the wave shape information.

The pulsation information may be a contraction speed or a relaxation speed of the pulsations of the cultured cardiomyocytes within the observation field, calculated on the basis of the wave shape information.

The pulsation information may be a correlation coefficient of a wave shape of the pulsations between the partial areas of the cultured cardiomyocytes within the observation field, calculated on the basis of the wave shape information.

The pulsation information may be a propagation speed and a propagation direction of the pulsations of the cultured cardiomyocytes within the observation field, calculated on the basis of the wave shape information.

The evaluation section may calculate the evaluation value that corresponds to each of the plurality of observation fields, before and after predetermined processing performed on the cultured cardiomyocytes, and the observation field determining section may determine the observation field by selecting a predetermined number of observation fields from the plurality of observation fields on the basis of a difference between the evaluation values before and after the predetermined processing performed on the cultured cardiomyocytes.

According to the first aspect of the present technology, there is provided a cell evaluation method including: detecting, by a motion detecting section, motion of cultured cardiomyocytes for each of partial areas of a plurality of observation fields on the cultured cardiomyocytes; calculating, by a motion amount calculating section, a motion amount of the detected motion; calculating, by a pulsation information calculating section, pulsation information on a characteristic amount of pulsations of the cultured cardiomyocytes on the basis of the calculated motion amount; calculating, by an evaluation value calculating section, an evaluation value corresponding to the plurality of observation fields, calculated on the basis of the pulsation information; and determining, by a field determining section, an observation field to be observed on the cultured cardiomyocytes, on the basis of the evaluation value.

According to the first aspect of the present technology, there is provided a program causing a computer to function as a cell evaluation apparatus including: a motion detecting section configured to detect motion of cultured cardiomyocytes for each of partial areas of a plurality of observation fields on the cultured cardiomyocytes; a motion amount calculating section configured to calculate a motion amount of the detected motion; a pulsation information calculating section configured to calculate pulsation information on a characteristic amount of pulsations of the cultured cardiomyocytes on the basis of the calculated motion amount; an evaluation value calculating section configured to calculate an evaluation value corresponding to the plurality of observation fields, calculated on the basis of the pulsation information; and a field determining section configured to determine an observation field to be observed on the cultured cardiomyocytes, on the basis of the evaluation value.

In the first aspect of the present technology, motion of cultured cardiomyocytes is detected for each of partial areas of a plurality of observation fields on the cultured cardiomyocytes, a motion amount of the detected motion is calculated, pulsation information that is information on a characteristic amount of pulsations of the cultured cardiomyocytes is calculated on the basis of the calculated motion amount, an evaluation value that is calculated on the basis of the pulsation information and corresponds to each of the plurality of observation fields is calculated, and an observation field to be observed on the cultured cardiomyocytes is determined on the basis of the evaluation value.

Effects of the Invention

According to the present technology, it is possible to easily search for an area to be observed in cardiomyocytes without requiring special preparation.

MODE(S) FOR CARRYING OUT THE INVENTION

Hereinafter, embodiments of the technology disclosed herein will be described with reference to the drawings.

For example, in regenerative medicine, cultured cells, which serve as cellular tissues produced by culturing cells that are collected from a living body, are used to treat various kinds of tissues and organs of human bodies. Cultured cardiomyocytes that are cultured cells obtained by culturing cardiomyocytes have a possibility of being used in treatment of heart, for example. Further, the cultured cardiomyocytes are also used for evaluation of toxicity to heart in drug development.

In a living body, the cardiomyocytes pulsate while constantly repeating contraction and relaxation. Therefore, in the cardiomyocytes, cells of each part thereof move in a predetermined direction such that the entire cardiomyocytes repeat contraction and relaxation. Actually, the cardiomyocytes have parts that autonomously pulsate and parts that pulsate depending on surrounding pulsations.

Figure 1:
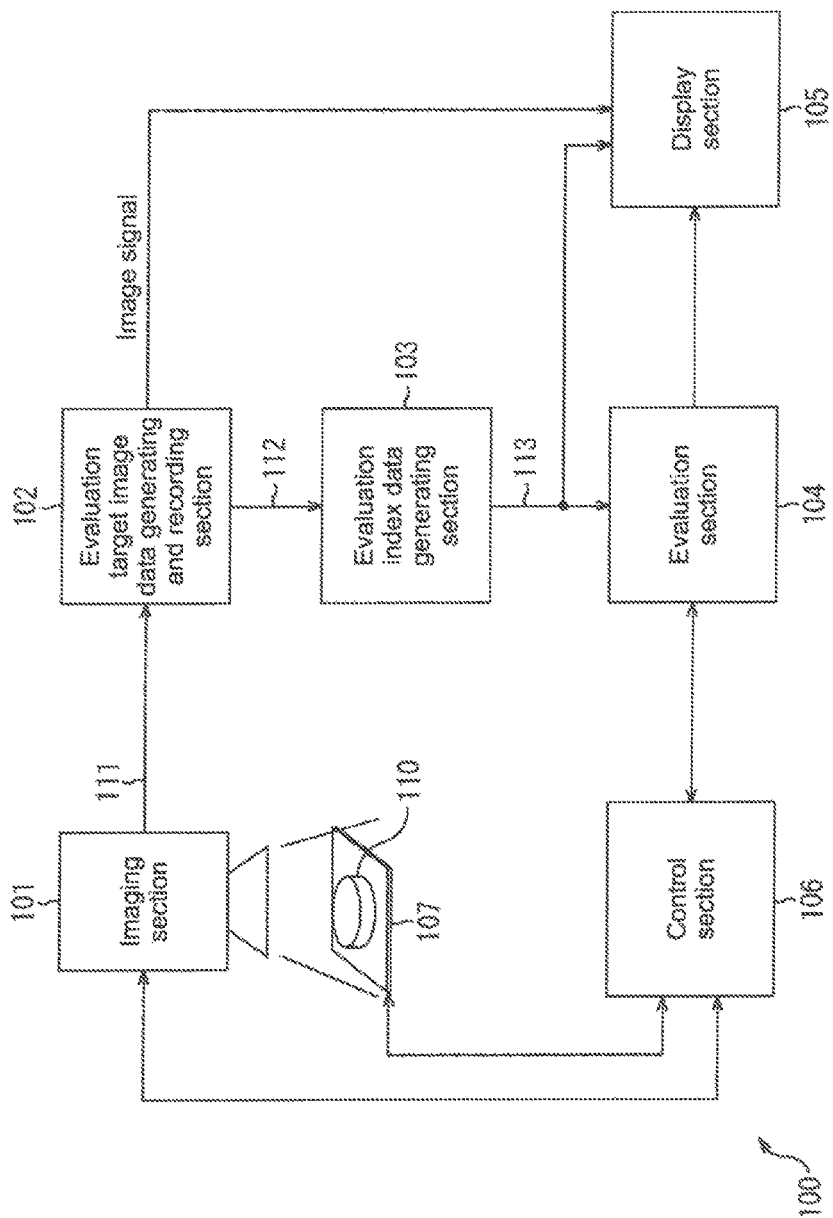
FIG. 1 is a block diagram showing a configuration example of a medication evaluation apparatus according to one embodiment of the present technology.

FIG. 1 is a block diagram showing a configuration example of a medication evaluation apparatus according to an embodiment of the present technology.

A medication evaluation apparatus 100 shown in the figure is an apparatus that observes motion of cultured cardiomyocytes 110 to evaluate a medication administered for the cultured cardiomyocytes 110. The medication evaluation apparatus 100 includes an imaging section 101, an evaluation target image data generating and recording section 102, an evaluation index data generating section 103, an evaluation section 104, a display section 105, a control section 106, and a stage 107.

The imaging section 101 images the cultured cardiomyocytes 110 as an observation target. The imaging section 101 may image the cultured cardiomyocytes 110 directly (without intervention of another member) or may image the cultured cardiomyocytes 110 via another member such as a microscope.

Further, the cultured cardiomyocytes 110 are placed on the stage 107 and fixed with respect to the imaging section 101. The stage 107 is configured to move under the control of the control section 106 in vertical and horizontal directions, for example.

The imaging section 101 images the cultured cardiomyocytes 110 for a predetermined period of time. Specifically, the imaging section 101 obtains a moving image in which the cultured cardiomyocytes 110 serve as a subject. The imaging section 101 images the cultured cardiomyocytes 110 before and after the administration of a medication. It should be noted that the imaging section 101 may image the cultured cardiomyocytes 110 more than once after the administration of a medication according to a predetermined condition, for example, each time a predetermined period of time elapses.

It should be noted that the imaging section 101 normally images a partial area of the cultured cardiomyocytes 110. By the movement of the stage 107 or the movement of the imaging section 101, an area to be imaged is moved in the cultured cardiomyocytes 110. An area to be imaged by the imaging section 101 at a predetermined time is called an observation field.

The imaging section 101 supplies an image signal 111 (moving image) of the image of the cultured cardiomyocytes 110, which is obtained by imaging, to the evaluation target image data generating and recording section 102.

The evaluation target image data generating and recording section 102 generates evaluation target image data on the basis of the image signal supplied from the imaging section 101 and records and saves the generated evaluation target image data in, for example, an internal recording medium. The evaluation target image data generated here is, for example, moving image data generated from the image signal obtained by imaging of the cultured cardiomyocytes 110.

For example, the evaluation target image data generating and recording section 102 may extract only frame images in a certain period of time from a plurality of frame images supplied from the imaging section 101 and use those frame images as the evaluation target image data. Further, for example, the evaluation target image data generating and recording section 102 may extract a partial area of each of the frame images supplied from the imaging section 101 as a small frame image and use a moving image including those small frame images as the evaluation target image data.

Moreover, for example, the evaluation target image data generating and recording section 102 may perform arbitrary image processing on each of the frame images supplied from the imaging section 101 and use a result of the image processing as the evaluation target image data. For the image processing, for example, enlargement, contraction, rotation, and deformation of images, correction of luminance and chromaticity, sharpness, noise removal, intermediate frame image generation, and the like may be considered. As a matter of course, any image processing other than those above may be employed.

The evaluation target image data generating and recording section 102 supplies the stored evaluation target image data 112 to the evaluation index data generating section 103 at a predetermined timing or in response to a request from the evaluation index data generating section 103.

The evaluation index data generating section 103 performs motion detection of the observation target (cultured cardiomyocytes 110) for each of the blocks, which are partial areas into which the entire area of the image of the observation target (cultured cardiomyocytes 110) is divided, between the frame images of the supplied evaluation target image data 112.

The evaluation index data generating section 103 expresses the detected motion of each of the blocks as a motion vector and obtains the magnitude of that motion vector (motion amount). Further, the evaluation index data generating section 103 calculates pulsation information that is information on a characteristic amount related to the pulsations of the cultured cardiomyocytes 110.

The evaluation index data generating section 103 supplies data containing the pulsation information, as evaluation index data 113, to the evaluation section 104.

The evaluation section 104 calculates an evaluation value related to each of the areas in the cultured cardiomyocytes 110 on the basis of the evaluation index data 113. Here, the evaluation value calculated by the evaluation section 104 is used to specify an area to be observed in the cultured cardiomyocytes 110, for example.

The display section 105 makes visible and displays the evaluation index data 113 and information related to the evaluation value generated by the evaluation section 104.

The control section 106 controls the movement of the stage 107 and controls imaging by the imaging section 101 on the basis of information output from the evaluation section 104. In other words, the control section 106 specifies an observation field in the cultured cardiomyocytes 110 on the basis of the information output from the evaluation section 104, and controls the stage 107 or the imaging section 101 such that an area corresponding to the observation field is imaged.

Figure 2:
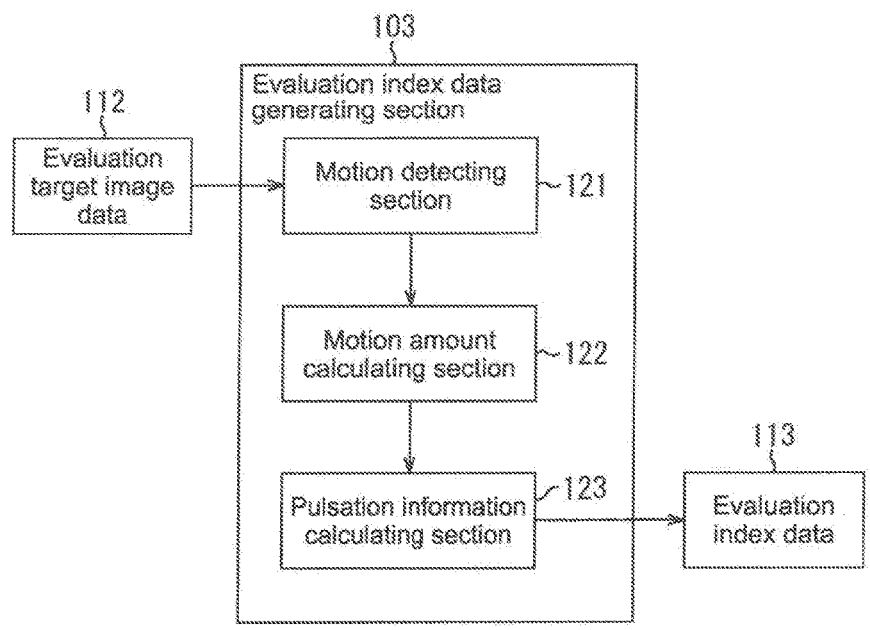
FIG. 2 is a block diagram showing a configuration example of an evaluation index data generating section of FIG. 1.

FIG. 2 is a block diagram showing a configuration example of the evaluation index data generating section 103 of FIG. 1. As shown in FIG. 2, the evaluation index data generating section 103 includes a motion detecting section 121, a motion amount calculating section 122, and a pulsation information calculating section 123.

The motion detecting section 121 inputs the recorded evaluation target image data 112 from the evaluation target image data generating and recording section 102 and performs motion detection for each of the blocks, to supply a result of the detection (motion vector) as motion detection data to the motion amount calculating section 122. The motion detection data will be described later.

As will be described later, the motion amount calculating section 122 divides each piece of the supplied motion detection data into new blocks and calculates an average motion amount in each of the blocks. The motion amount calculating section 122 supplies the calculated average motion amount to the pulsation information calculating section 123.

The pulsation information calculating section 123 calculates pulsation information, which will be described later, at a predetermined timing or in response to a request from the evaluation section 104, and generates the evaluation index data 113 containing that pulsation information. The generated evaluation index data 113 is supplied to the evaluation section 104.

It should be noted that the motion detecting section 121, the motion amount calculating section 122, and the pulsation information calculating section 123 perform the above processing for each of the frame images of the evaluation target image data.

Figure 3:
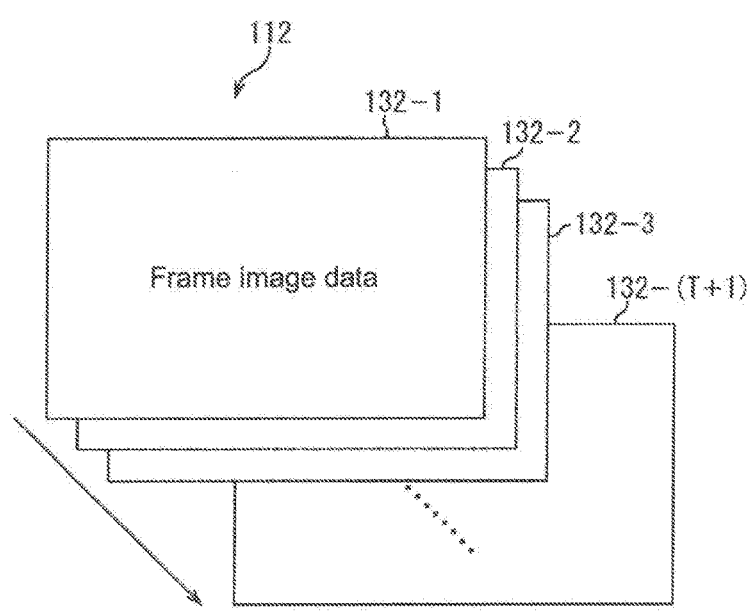
FIG. 3 is a diagram showing a structural example of evaluation target image data supplied to the evaluation index data generating section.

FIG. 3 shows a structural example of the evaluation target image data 112 supplied to the evaluation index data generating section 103. Imaging is performed in an evaluation interval having a predetermined length (for example, T+1 frames (T is an arbitrary natural number)). Specifically, the evaluation target image data 112 supplied to the evaluation index data generating section 103 is constituted by, for example, the first to (T+1)th frame image data 132-1 to 132-(T+1) corresponding to the evaluation interval.

Figure 4:
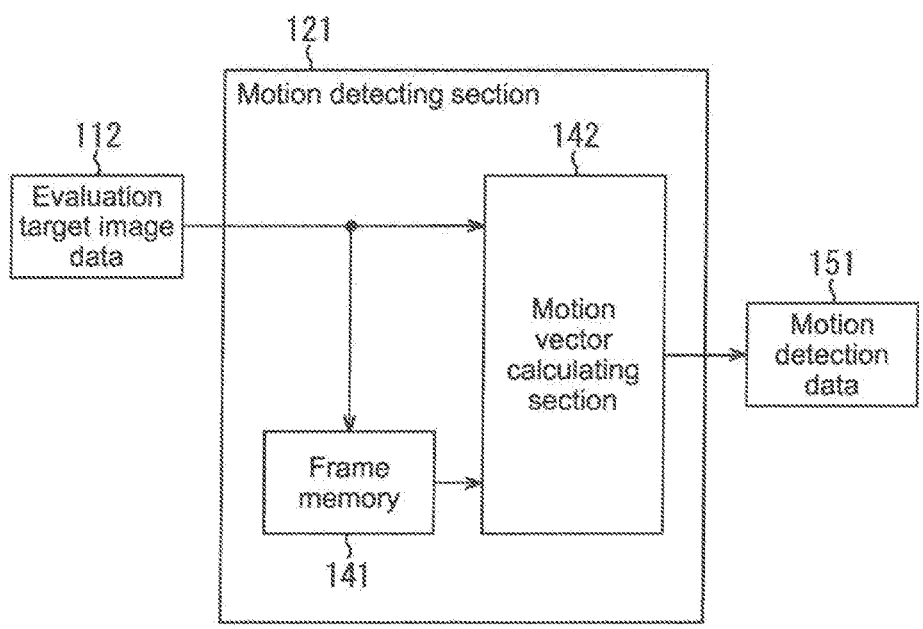
FIG. 4 is a block diagram showing a configuration example of a motion detecting section of FIG. 2.

FIG. 4 is a block diagram showing a main configuration example of the motion detecting section 121. As shown in FIG. 4, the motion detecting section 121 includes a frame memory 141 and a motion vector calculating section 142. The frame memory 141 retains the pieces of frame image data 132, which are sequentially input thereto as the evaluation target image data 112 per frame period.

The motion vector calculating section 142 inputs the frame image data that is input as the evaluation target image data 112 of a current time, and the frame image data of the latest (chronologically earlier) time that is retained in the frame memory 141. The motion vector calculating section 142 then calculates a motion vector for each of the blocks, the motion vector indicating motion between those two pieces of frame image data. The calculated motion vector is supplied to the motion amount calculating section 122 as motion detection data 151.

Figure 5:
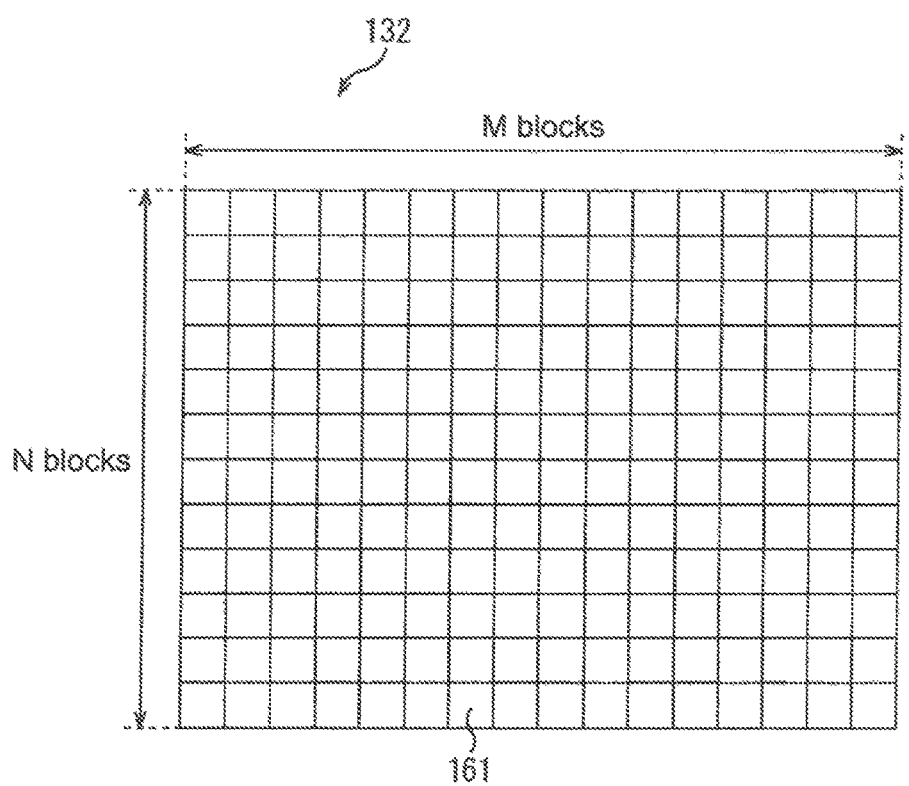
FIG. 5 is a diagram showing a configuration example of frame image data.

The processing executed by the motion detecting section 121 of FIG. 4 will be described in more detail. The motion vector calculating section 142 inputs the frame image data 132 of the current time and the frame image data 132 of the latest (chronologically earlier) time. The motion vector calculating section 142 divides each piece of the input frame image data 132 into M×N (M and N are each an arbitrary natural number) blocks 161 as shown in FIG. 5, and performs motion detection for each of the blocks 161 by a technique such as block matching between the frame images, for example, to generate a motion vector.

The motion vector calculating section 142 executes such motion detection processing by sequentially using the first to (T+1)th frame image data 132. Specifically, the motion vector calculating section 142 generates (M×N×T) pieces of motion detection data (motion vectors) using the (T+1) frame images. The motion vector calculating section 142 supplies the motion vectors thus calculated, which serve as motion detection data, to the motion amount calculating section 122.

Figure 6:
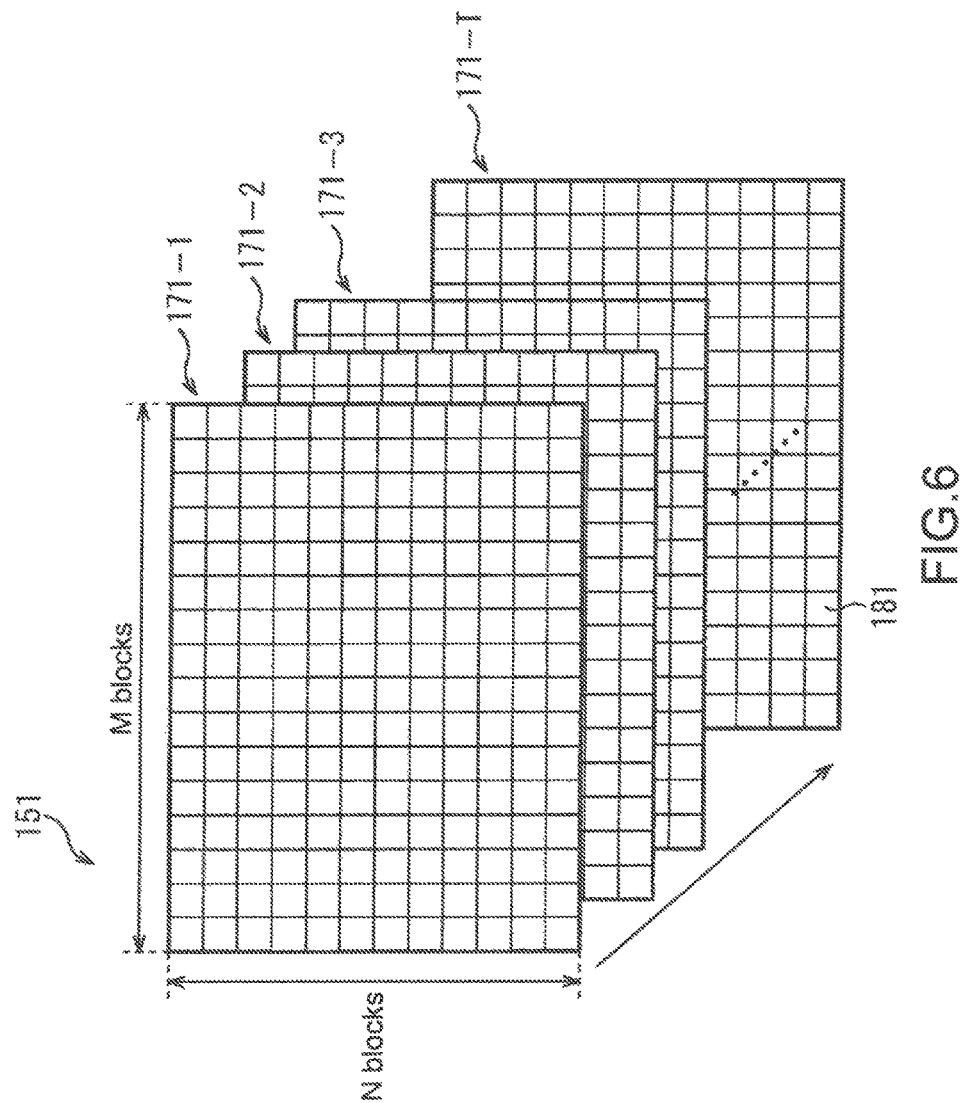
FIG. 6 is a diagram showing a configuration example of motion detection data.

When the final motion detection processing using the Tth and (T+1)th frame image data 132 is completed, as shown in FIG. 6, motion detection data constituted by T pieces of frame unit motion detection data 171-1 to 171-T are supplied to the motion amount calculating section 122.

Each piece of the frame unit motion detection data 171-1 to 171-T is obtained by performing the motion detection processing on the frame image data 132 of the current time, which is obtained per frame period, and on the frame image data 132 of the latest (chronologically earlier) time.

For example, the third frame unit motion detection data 171-3 is obtained by inputting the fourth frame image data 132-4 and the third frame image data 132-3 as the frame image data of the current time and the frame image data of the latest time, respectively, and performing the motion detection.

Further, each piece of the frame unit motion detection data 171-1 to 171-T is constituted by (M×N) pieces of block unit motion detection data 181. Each piece of the block unit motion detection data 181 corresponds to one block 161 and is to be data indicating a motion vector detected for a corresponding block 161.

As described above, the motion detection data 151 of this embodiment has a structure including the (M×N) pieces of block unit motion detection data 181 in each piece of the frame unit motion detection data 171.

Figure 7:
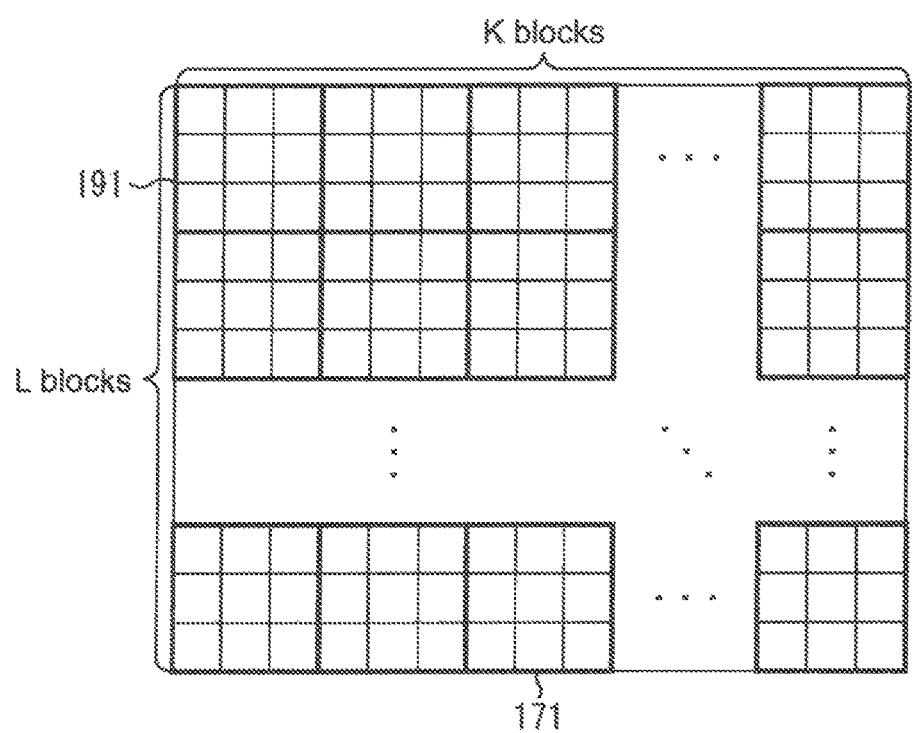
FIG. 7 is a diagram for describing processing of a motion amount calculating section.
Figure 8:
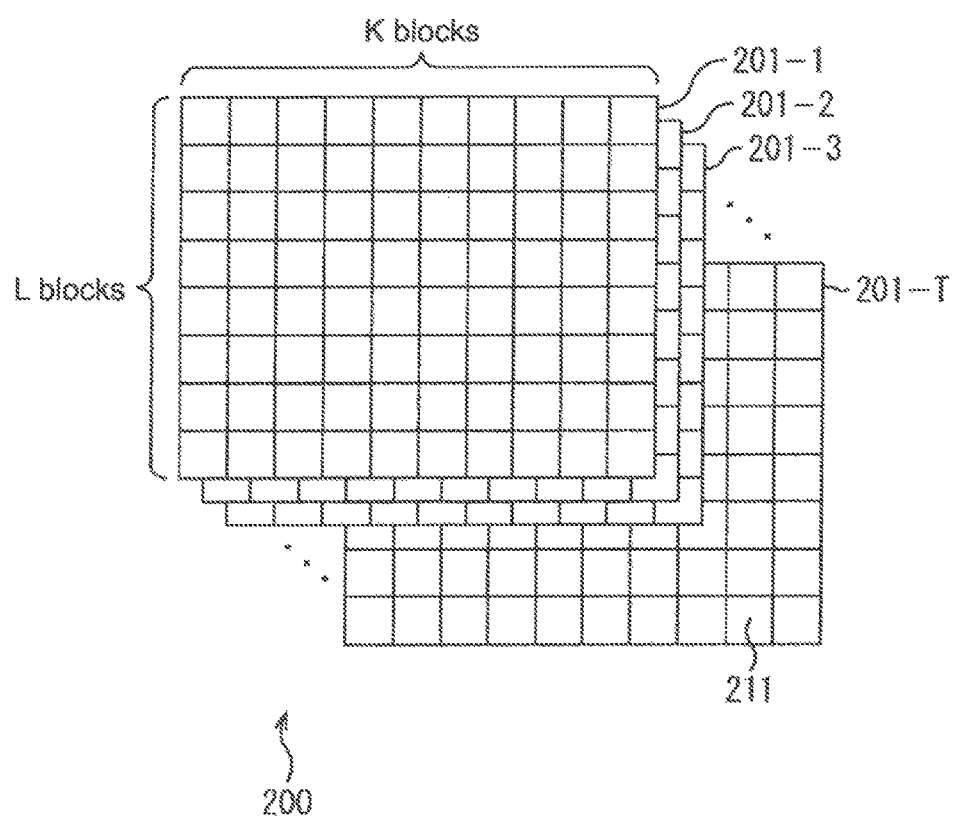
FIG. 8 is a diagram for describing processing of the motion amount calculating section.

FIGS. 7 and 8 are diagrams for describing the processing executed by the motion amount calculating section 122.

In the motion detection data 151, the motion amount calculating section 122 newly divides each piece of the frame unit motion detection data 171, which is constituted by the (M×N) blocks, into (K×L) blocks. For example, as shown in FIG. 7, the frame motion detection data 171 is divided into (K×L) blocks 191.

The motion amount calculating section 122 calculates an average value of the pieces of block unit motion detection data 181 included in each of the (K×L) blocks 191, to calculate an average motion amount in each block. For example, in the case where L=N/3 and K=M/3, an average value of the nine motion vectors (block unit motion detection data 181) within the block 191 is calculated, and (K×L) average motion amounts are calculated.

As will be described later, the values of K and L may vary depending on the pulsation information calculated by the pulsation information calculating section 123. For example, when a pulsation area is calculated by the pulsation information calculating section 123, it is assumed that L=N and K=M. Further, for example, when the number of pulsations is calculated by the pulsation information calculating section 123, it is assumed that L=1 and K=1 (i.e., one for the entire screen). Furthermore, when a correlation coefficient is calculated by the pulsation information calculating section 123, it is assumed that L=4 and K=4 (i.e., the entire screen is divided into 4×4). Moreover, for example, when a propagation speed and a propagation direction per pulsation are calculated by the pulsation information calculating section 123, it is assumed that L=8 and K=8 (i.e., the entire screen is divided into 8×8).

Thus, for example, as shown in FIG. 8, motion amount data 200 constituted by T pieces of frame unit motion amount data 201-1 to 201-T is generated. As described above, each piece of the frame unit motion amount data 201-1 to 201-T is constituted by (K×L) pieces of block unit motion amount data 211. Each piece of the block unit motion amount data 211 corresponds to one block 191 and is to be data indicating an average value of the motion vectors within a corresponding block 191.

Next, an example of the processing of the pulsation information calculating section 123 will be described. The pulsation information calculating section 123 calculates the pulsation information, which is information on a characteristic amount related to the pulsations of cultured cardiomyocytes, in the following manner, for example.

The pulsation information calculating section 123 calculates a pulsation area within an observation field.

For example, the pieces of block unit motion amount data 211, which correspond to a predetermined number of frames, are added, and thus the presence or absence of pulsations within a unit time is determined. For example, the pieces of block unit motion amount data 211 of the blocks 191 of the frame unit motion amount data 201-1 to 201-J (J<T) are added. An added value of the pieces of block unit motion amount data corresponding to the respective blocks 191 is compared with a threshold value, and the blocks 191 having an added value smaller than the threshold value are determined to have no pulsations within a unit time.

In such a manner, an area corresponding to the number of blocks 191 within the observation field, which excludes the blocks 191 having no pulsations within a unit time, is calculated as a pulsation area.

The pulsation area calculated in such a manner is assumed to be one type of pulsation information calculated by the pulsation information calculating section 123.

Further, the pulsation information calculating section 123 calculates the number of pulsations within the observation field.

The pulsation information calculating section 123 generates wave shape information 220 indicating a change in motion amount on the basis of the motion amount data 200. In other words, the pulsation information calculating section 123 averages the (K×L) pieces of block unit motion amount data 211, which form the motion amount data 200, over the entire screen and thus calculates a change with time in the observation field.

Figure 9:
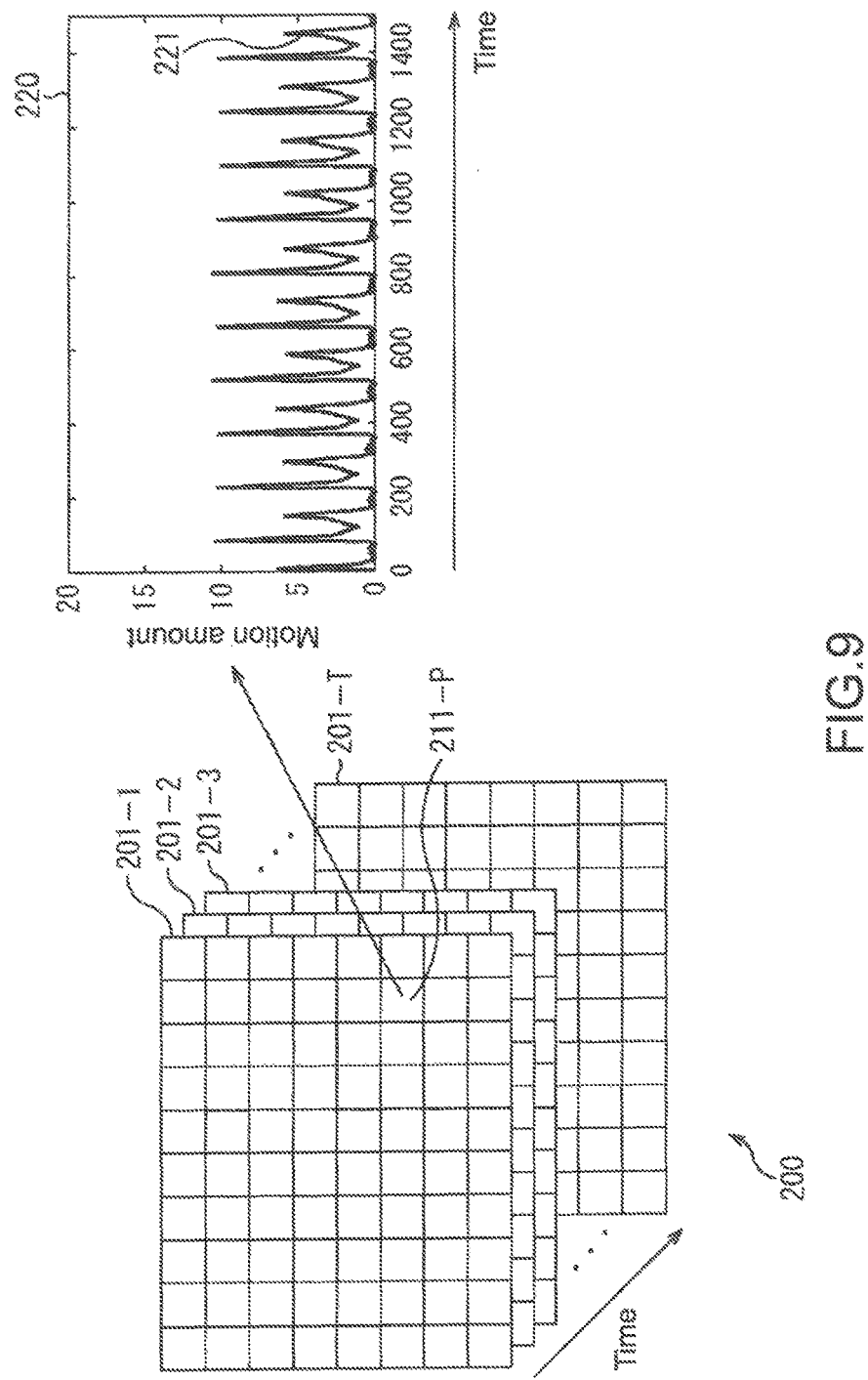
FIG. 9 is a diagram for describing processing of a pulsation information calculating section.

For example, as shown in FIG. 9, an average value of the pieces of block unit motion amount data in the pieces of frame unit motion amount data 201-1 to 201-1 on the entire screen is plotted for each time, the frame unit motion amount data 201-1 to 201-T forming the motion amount data 200. Thus, the wave shape information 220 for the observation field is generated. In the wave shape information 220 in FIG. 9, the horizontal axis represents a time, the vertical axis represents a motion amount, and a change with time in average value of the motion amounts within the observation field is denoted as wave shapes 221.

The pulsation information calculating section 123 specifies a rise time of each wave shape in the wave shape information 220. The wave shapes 221 in FIG. 9 are assumed as wave shapes in which high peaks and low peaks alternately appear. This is because contraction and relaxation are repeated in the pulsations of the cultured cardiomyocytes. The high peaks correspond to times at which the cultured cardiomyocytes contract, and the low peaks correspond to times at which the cultured cardiomyocytes relax.

It should be noted that the peaks corresponding to the contraction of the cultured cardiomyocytes and the peaks corresponding to the relaxation thereof can be distinguished on the basis of the following characteristics, for example. In the wave shapes of pulsations, the contraction peaks are prior to the relaxation peaks. Further, the contraction peaks have a higher speed. Furthermore, the contraction peaks have a sharper rise. Moreover, the contraction peaks have a lower speed of the starting point.

Therefore, it is possible to recognize that a period of time from the rise of the contraction peak to the fall of the relaxation peak, which is indicated by the wave shape 221, is one pulsation of the cultured cardiomyocytes of an appropriate block. On the basis of the wave shapes 221 of the wave shape information 220, the number of pulsations within a unit time in the block can be calculated.

The pulsation information calculating section 123 calculates an average value on the number of pulsations in each of the blocks 191 within the observation field, for example, and sets the average value to be the number of pulsations within the observation field.

The number of pulsations calculated in such a manner is assumed as one type of the pulsation information calculated by the pulsation information calculating section 123.

Further, the pulsation information calculating section 123 calculates a contraction time and a relaxation time of the pulsations within the observation field.

For example, the contraction time is calculated as a period of time from the rise of a contraction peak to the reach of the fall of the contraction peak in the wave shape 221 of the wave shape information 220. Further, for example, the relaxation time is calculated as a period of time from the rise of a relaxation peak to the reach of the fall of the relaxation peak in the wave shape 221 of the wave shape information 220. It should be noted that the contraction time may be calculated using a period of time from the rise of a contraction peak to the reach of the fall of a relaxation peak.

The pulsation information calculating section 123 sets, for example, an average value of the contraction times and the relaxation times within a predetermined period of time to be a contraction time and a relaxation time within the observation field.

The contraction time and the relaxation time calculated in such a manner are one type of the pulsation information calculated by the pulsation information calculating section 123.

Moreover, the pulsation information calculating section 123 calculates a contraction speed and a relaxation speed of the pulsations within the observation field.

For example, the contraction speed is calculated on the basis of a period of time from the rise of a contraction peak to the reach to the peak in the wave shape 221 of the wave shape information 220 and on the basis of a motion amount corresponding to the contraction peak. Further, for example, the relaxation speed is calculated on the basis of a period of time from the rise of a relaxation peak to the reach to the peak in the wave shape 221 of the wave shape information 220 and on the basis of a motion amount corresponding to the relaxation peak.

The pulsation information calculating section 123 sets, for example, an average value of the contraction speeds and the relaxation speeds within a predetermined period of time to be a contraction speed and a relaxation speed within the observation field.

The contraction speed and the relaxation speed calculated in such a manner are one type of the pulsation information calculated by the pulsation information calculating section 123.

Further, the pulsation information calculating section 123 calculates a pulsation duration time within the observation field. The pulsation duration time is calculated as, for example, a period of time from the rise of a contraction peak to the reach of the fall of a relaxation peak in the wave shape 221 of the wave shape information 220.

Further, the pulsation information calculating section 123 calculates a correlation coefficient between blocks within the observation field.

For example, the pulsation information calculating section 123 sets blocks for which a correlation coefficient is to be calculated. For example, a block 191-A and a block 191-B are set as blocks for which a correlation coefficient is to be calculated.

Figure 10:
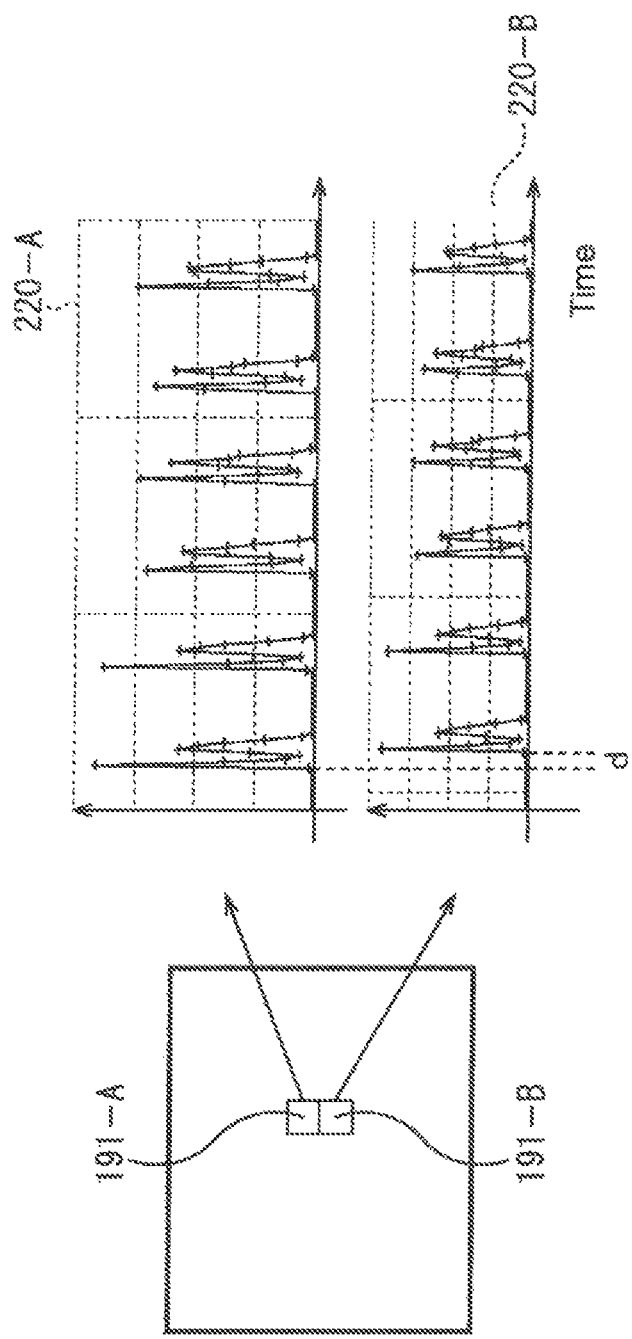
FIG. 10 is a diagram for describing processing of the pulsation information calculating section.

Further, the pulsation information calculating section 123 obtains the wave shape information 220, which is as described above with reference to FIG. 9, for each of the blocks 191-A and 191-B. For example, as shown in FIG. 10, wave shape information 220-A and wave shape information 220-B are obtained for the block 191-A and the block 191-B, respectively, the block 191-A and the block 191-B being adjacent to each other.

The pulsation information calculating section 123 obtains a correlation coefficient of the pulsations of the blocks 191-A and 191-B. Such a correlation coefficient is a parameter indicating cooperative performance of the pulsations and has a larger value as the cooperative performance between the blocks becomes higher.

For example, the pulsation information calculating section 123 calculates a correlation coefficient between the motion of the block 191-A and the motion of the block 191-B, for example. In other words, the pulsation information calculating section 123 calculates a correlation coefficient by using the motion amounts of the block 191-1A and the block 191-B of a frame of a specific time, and an average value of the motion amounts of the block 191-A and the block 191-B in a chronological direction within an appropriate evaluation interval. Specifically, a degree of correlation between the two blocks in a state of a change in motion amount within the evaluation interval is calculated.

The pulsation information calculating section 123 obtains such a correlation coefficient, for example, between arbitrary blocks 191 within the observation field roughly throughout and over the entire screen or within a predetermined vicinity area, and calculates an average value of the correlation coefficients.

The correlation coefficient calculated in such a manner is assumed as one type of the pulsation information calculated by the pulsation information calculating section 123.

Moreover, the pulsation information calculating section 123 calculates a propagation speed and a propagation direction of the pulsations within the observation field as follows.

Figure 11:
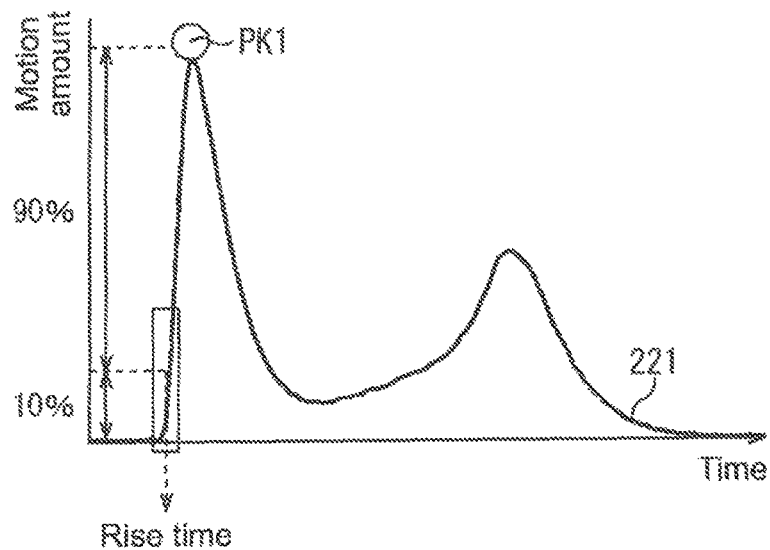
FIG. 11 is a diagram for describing processing of the pulsation information calculating section.

FIG. 11 is an enlarged diagram of a portion of the wave shape 221 of FIG. 9. At that time, the pulsation information calculating section 123 sets a motion amount of a high peak (i.e., a peak corresponding to contraction of the cultured cardiomyocytes) PK1 as 100%, and specifies a time at which the wave shape reaches 10% of the motion amount of the peak PK1 as a rise time Tup.

Figure 12:
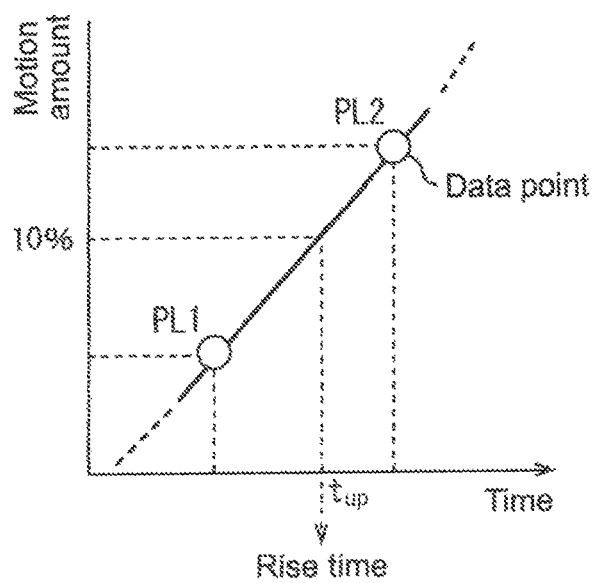
FIG. 12 is a diagram for describing processing of the pulsation information calculating section.

When there is no plotted point in the wave shape 221, the plotted point corresponding to the time at which the wave shape reaches 10% of the motion amount of the peak PK1, for example, the wave shape is interpolated on the basis of the previous and next plotted points, to specify the rise time Tup. FIG. 12 is an enlarged diagram of the vicinity of the rise of the wave shape 221 in FIG. 11 (a portion surrounded by the rectangular shape in the figure). In the figure, the wave shape is interpolated on the basis of plotted points PL1 and PL2.

In such a manner, the rise time of a block 191-$p$ corresponding to block unit motion amount data 211-$p$ is specified. The rise time of a block around the block 191-$p$ is also specified.

Figure 13:
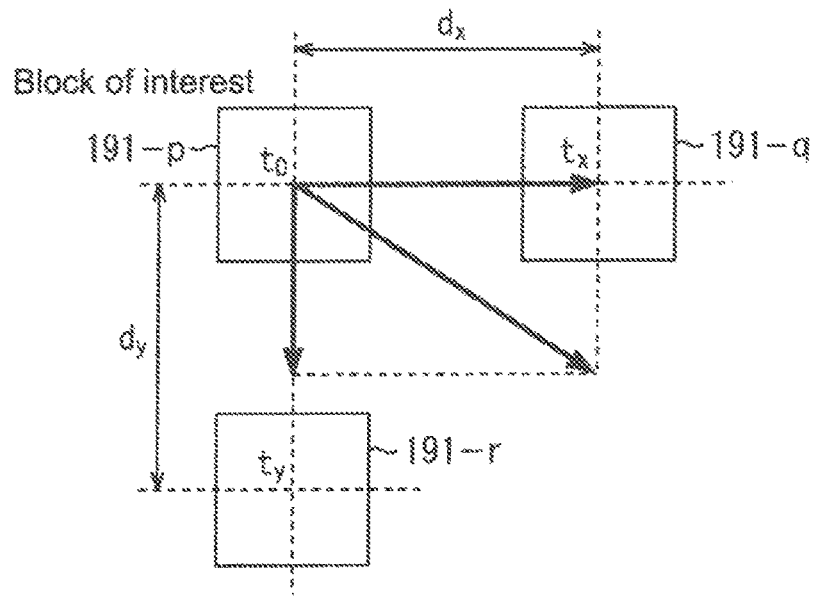
FIG. 13 is a diagram for describing processing of the pulsation information calculating section.

For example, as shown in FIG. 13, the pulsation information calculating section 123 sets a block of interest in each of the (K×L) blocks 191. For example, the block 191-$p$ is set as a block of interest, and a rise time t0 of the first pulsation of the block of interest 191-$p$ is specified. A rise time tx of the first pulsation of a block 191-$q$ that is separated from the block of interest by a predetermined distance (for example, a distance corresponding to two blocks) in the horizontal direction is then specified, and a rise time ty of the first pulsation of a block 191-$r$ that is separated from the block of interest by a predetermined distance (for example, a distance corresponding to two blocks) in the vertical direction is further specified.

The pulsation information calculating section 123 obtains a propagation speed vx of a pulsation in the horizontal direction and a propagation speed vy of a pulsation in the vertical direction by Expression (1).

[Expression 1]

$$v_x = \frac{d_x}{t_x - t_0},$$
$$v_y = \frac{d_y}{t_y - t_0} \quad (1)$$

Further, the pulsation information calculating section 123 obtains a propagation speed |v| of a pulsation by Expression (2) on the basis of the propagation speed vx of a pulsation in the horizontal direction and the propagation speed vy of a pulsation in the vertical direction.

[Expression 2]

$$|v| = \sqrt{v_x^2 + v_y^2} \quad (2)$$

Moreover, the pulsation information calculating section 123 obtains a propagation direction θ of a pulsation by Expression (3) on the basis of the propagation speed vx of a pulsation in the horizontal direction and the propagation speed vy of a pulsation in the vertical direction.

[Expression 3]

$$\theta = \tan^{-1} \frac{v_y}{v_x} \quad (3)$$

In such a manner, the propagation speed and the propagation direction of the block 191-$p$ are calculated. Further, similarly, a propagation speed and a propagation direction of another block as a block of interest are calculated.

In such a manner, the propagation speeds and the propagation directions of the pulsations of the cultured cardiomyocytes are calculated. It should be noted that the propagation speed and the propagation direction obtained here are obtained per pulsation for each of the blocks of the motion amount data 200. The propagation speed and the propagation direction per pulsation in each block, for example, the propagation speed and the propagation direction of the first pulsation in the block 191-$p$, the propagation speed and the propagation direction of the second pulsation therein, the propagation speed and the propagation direction of the third pulsation therein, . . . , the propagation speed and the propagation direction of the first pulsation in a block 191-$p$+1, the propagation speed and the propagation direction of the second pulsation therein, the propagation speed and the propagation direction of the third pulsation therein, . . . , are obtained.

The propagation speeds and the propagation directions of the respective pulsations calculated in such a manner are assumed as one type of the pulsation information calculated by the pulsation information calculating section 123.

Further, information representing the orientation of the pulsations in the observation field may be calculated as one type of pulsation information.

The data obtained in such a manner, which contains the pulsation information on the observation field, is output as the evaluation index data 113.

As described above, after the pulsation information is calculated for one observation field, the pulsation information calculating section 123 calculates pulsation information on the next observation field.

For example, when the calculation of the pulsation information on one observation field is completed, the stage 107 is moved on the basis of a control signal that is output from the control section 106, and an area that corresponds to the next observation field and is a partial area in the cultured cardiomyocytes 110 is imaged by the imaging section 101. The pulsation information on the next observation field is then calculated.

Figure 14:
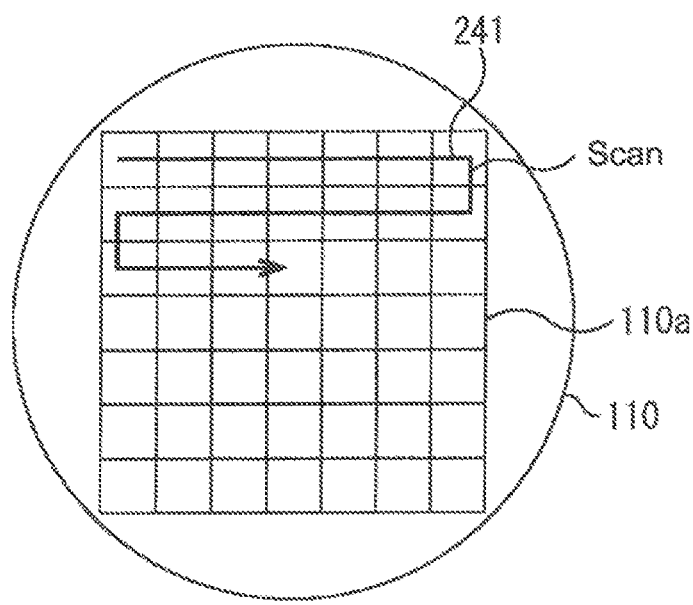
FIG. 14 is a diagram for describing processing of a control section.

FIG. 14 is a diagram for describing a mode in which the observation field is moved by the movement of the stage 107 under the control of the control section 106. A circle of the figure represents the cultured cardiomyocytes 110 (actually, a culture dish, a well, etc. in which the cultured cardiomyocytes 110 are placed), and a rectangular area 110a within the circle may be an observation target.

For example, each small rectangle within the area 110a is assumed as an area corresponding to one observation field, and the movement of the stage 107 is controlled such that the observation field is moved as indicated by a line 241 in the figure.

In such a manner, the pulsation information is calculated in association with each of a plurality of observation fields.

Referring back to FIG. 1, an example of the processing of the evaluation section 104 will be described.

As described above, the evaluation section 104 calculates an evaluation value related to each area in the cultured cardiomyocytes 110 on the basis of the evaluation index data 113 containing the pulsation information.

Figure 15:
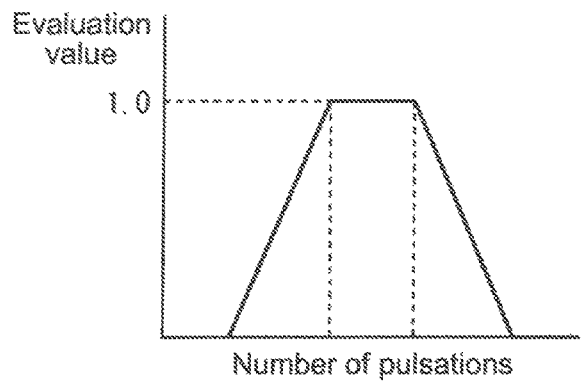
FIG. 15 is a diagram for describing processing of an evaluation section.

For example, the evaluation section 104 calculates an evaluation value E1. The evaluation value E1 evaluates that the number of pulsations within a unit time within an appropriate observation field falls within a certain range. The evaluation value E1 is obtained as shown in FIG. 15, for example. In FIG. 15, the horizontal axis represents the number of pulsations and the vertical axis represents the evaluation value. As shown in FIG. 15, when the number of pulsations falls within a certain range, the evaluation value is 1. When the number of pulsations is out of the certain range, the evaluation value is decreased.

Figure 16:
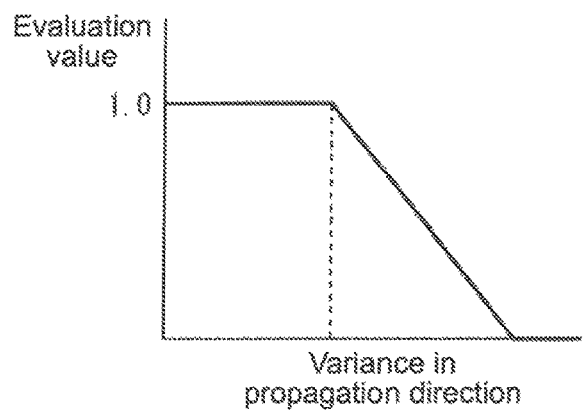
FIG. 16 is a diagram for describing processing of the evaluation section.

Further, for example, the evaluation section 104 calculates an evaluation value E2. The evaluation value E2 represents the smallness (degree of dispersion) of a dispersion value of an average value of the propagation direction related to the plurality of pulsations within that observation field. The evaluation value E2 is obtained as shown in FIG. 16, for example. In FIG. 16, the horizontal axis represents the dispersion value of the propagation direction and the vertical axis represents the evaluation value. As shown in FIG. 16, when a value of the horizontal axis is smaller than a predetermined threshold value, the evaluation value is 1. When a value of the horizontal axis is equal to or larger than the predetermined threshold value, the evaluation value is decreased.

Figure 17:
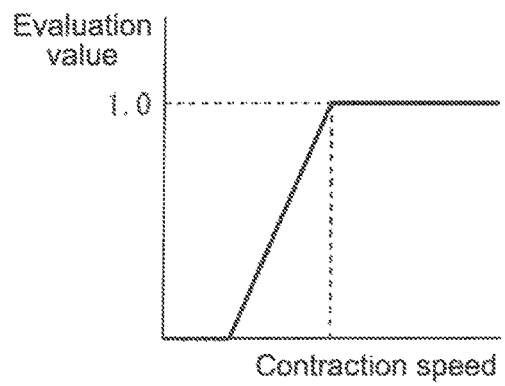
FIG. 17 is a diagram for describing processing of the evaluation section.

Further, for example, the evaluation section 104 calculates an evaluation value E3. The evaluation value E3 evaluates the magnitude of a contraction speed of the pulsations within the observation field. The evaluation value E3 is obtained as shown in FIG. 17, for example. In FIG. 17, the horizontal axis represents the contraction speed and the vertical axis represents the evaluation value. As shown in FIG. 17, when a value of the horizontal axis is equal to or larger than a predetermined threshold value, the evaluation value is 1. When the value of the horizontal axis is smaller than the predetermined threshold value, the evaluation value is decreased.

Similarly, an evaluation value E4, an evaluation value E5, . . . related to other pieces of pulsation information may be calculated by the evaluation section 104.

The evaluation section 104 then calculates an observation field evaluation value E that evaluates the importance of an area to be observed in the cultured cardiomyocytes 110.

For example, when the evaluation values E1 to E5 are calculated as described above, the evaluation values E1 to E5 are used to obtain the observation field evaluation value E that evaluates the importance of an area to be observed in the cultured cardiomyocytes 110 by Expression (4).

[Expression 4]

$$E = \alpha_1 E_1 + \alpha_2 E_2 + \alpha_3 E_3 + \alpha_4 E_4 + \alpha_5 E_5 \quad (4)$$

It should be noted that $\alpha 1$ to $\alpha 5$ in Expression (4) are assumed to be preset weight coefficients.

The control section 106 moves the stage 107 on the basis of the observation field evaluation value E, and thus an area having high importance as an area to be observed in the cultured cardiomyocytes is automatically set as an observation field.

The above embodiment has been described in which when the calculation of the pulsation information for one observation field is completed, the stage 107 is moved on the basis of the control signal output from the control section 106, and an area corresponding to the next observation field is imaged by the imaging section 101. However, for example, when the calculation of the observation field evaluation value for one observation field is completed, the stage 107 may be moved on the basis of the control signal output from the control section 106, and an area corresponding to the next observation field may be imaged by the imaging section 101.

Referring back to FIG. 1, an example of the processing of the display section 105 will be described.

The display section 105 makes visible and displays the evaluation index data 113 and the information related to the evaluation value generated by the evaluation section 104.

Figure 18:
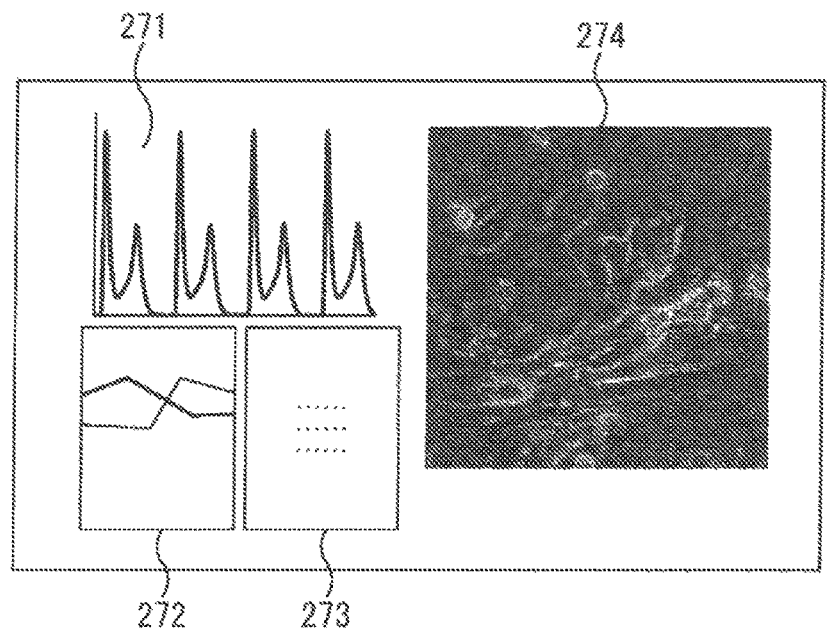
FIG. 18 is a diagram showing an example of information displayed by a display section.

FIG. 18 is a diagram showing an example of a screen that is displayed by the processing of the display section 105. In an area 271 on the upper left of the figure, wave shape information is displayed. The wave shape information displayed in the area 271 is displayed on the basis of, for example, the wave shape information 220 generated by the pulsation information calculating section 123.

Further, in an area 272 on the lower left of FIG. 18, the transition of the pulsation information with the elapse of time is displayed as a graph. In the area 272, for example, the transition of the pulsation information with the elapse of time, the pulsation information containing a contraction time, a contraction speed, a correlation coefficient, and the like, is displayed as a graph.

Further, in an area 273 on the right side of the area 272 of FIG. 18, the pulsation information is displayed using numerical values, characters, and the like. In the area 273, for example, the pulsation information calculated by the pulsation information calculating section 123 is displayed using numerical values or characters.

In an area 274 on the right side of FIG. 18, an image of the observation field is displayed. In other words, in the area 274, an image of an area of the cultured cardiomyocytes 110, which is taken by the imaging section 101, is displayed. The image may be a moving image or a still image.

Figure 19:
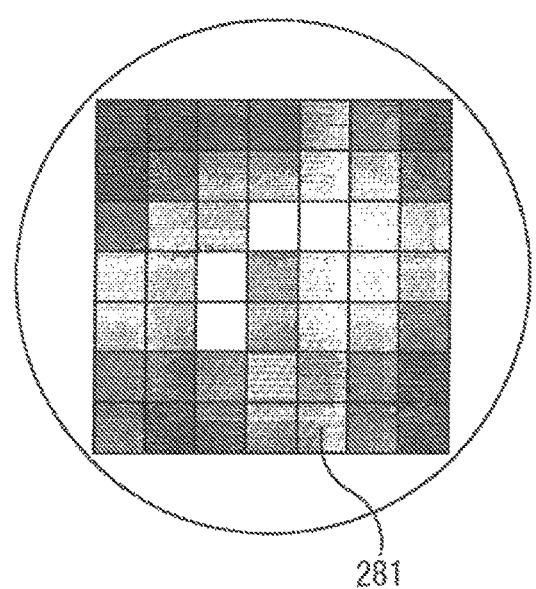
FIG. 19 is a diagram showing an example of an evaluation value map.

FIG. 19 is a diagram showing another example of the screen displayed by the processing of the display section 105. FIG. 19 shows an evaluation value map 281. The evaluation value map 281 shows, for example, the observation fields described with reference to FIG. 14, which are displayed in different colors on the basis of the observation field evaluation values E. In the evaluation value map 281, the rectangles corresponding to the respective observation fields are displayed in lighter colors as the observation field evaluation values E of the observation fields become larger, and are displayed in darker colors as the observation field evaluation values E of the observation fields become smaller, for example.

Further, the evaluation value map 281 is not necessarily displayed in different colors only on the basis of the observation field evaluation values E and, for example, may be displayed in different colors on the basis of any value of the evaluation values E1 to E5.

Further, for example, the control section 106 may select an observation field on the basis of the evaluation value map 281 to move the stage 107. For example, an observation field in which the observation field evaluation value E becomes maximum may be observed. Alternatively, the stage 107 may be moved such that N observation fields having the largest N observation field evaluation values E are sequentially observed.

Further, similarly, for example, an observation field in which any value of the evaluation values E1 to E5 becomes maximum may be observed. Alternatively, the stage 107 may be moved such that N observation fields having the largest N evaluation values, which are any values of various evaluation values including the evaluation value E1, the evaluation value E2, the evaluation value E3, and the like, are sequentially observed.

Alternatively, the stage 107 may be moved such that an observation field in which various kinds of evaluation values become maximum is observed among a plurality of observation fields selected in advance.

Alternatively, for example, the evaluation value map 281 displayed on a display may be used as a GUI (Graphical User Interface), and the stage 107 may be moved such that an observation field selected by the user is observed.

As described above, it is also possible to select an observation field on the basis of the evaluation value map 281.

As configured in such a manner, the user can easily specify the observation field.

In the above description, the example in which the cultured cardiomyocytes are placed in one culture dish, a well, and the like has been described. However, for example, on a well plate on which a plurality of wells is arranged, cultured cardiomyocytes placed on the respective wells may be observed.

Figure 20:
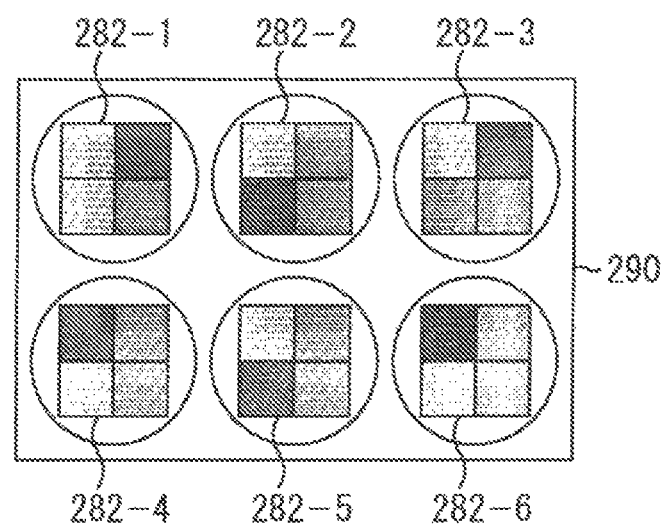
FIG. 20 is a diagram showing another example of the evaluation value map.

FIG. 20 is a diagram showing an example of an evaluation value map in the case where a well plate on which six wells are arranged is used. In this example, as shown by circles in the figure, six wells are arranged on a well plate 290 represented by a rectangular shape.

When the well plate shown in FIG. 20 is used, evaluation value maps 282-1 to 282-6 are generated to correspond to the respective six wells.

In this case, for example, the stage 107 may be moved such that the observation field is selected from the six wells on the basis of the evaluation value maps 282-1 to 282-6, as in the case described above.

Alternatively, for example, the observation field may be selected on the basis of a difference between the evaluation value previously calculated and the evaluation value most recently calculated.

For example, after the elapse of a predetermined period of time from the first calculation of the evaluation value, a second calculation of the evaluation value is performed. A difference between the evaluation value of the first time and the evaluation value of the second time may be calculated in each observation field and, for example, an observation field having a large difference may be selected. Alternatively, for example, a difference between the evaluation values may be calculated in each observation field before and after medication, and then an observation field having a large difference in evaluation values may be selected.

Similarly, for example, the observation field may be selected on the basis of a difference between the pulsation information previously calculated and the pulsation information most recently calculated.

As configured in such a manner, for example, an area in which pulsations are made stable by medication, an area in which pulsations are disturbed by medication, and the like can be easily searched for and observed.

Next, an example of observation field determination processing by the medication evaluation apparatus 100 to which the present technology is applied will be described with reference to a flowchart of FIG. 21.

In Step S21, the evaluation target image data generating and recording section 102 obtains image data of a taken image of cultured cardiomyocytes.

Figure 22:
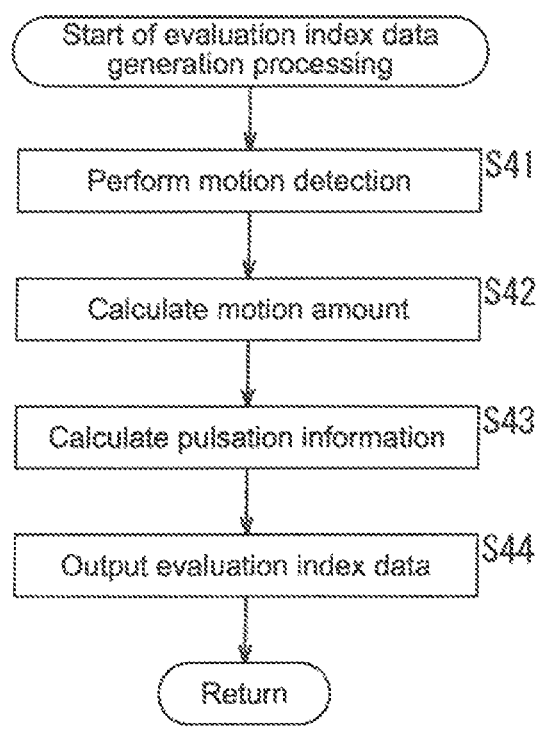
FIG. 22 is a flowchart for describing an example of evaluation index data generation processing.

In Step S22, the evaluation index data generating section 103 executes evaluation index data generation processing, which will be described later, with reference to a flowchart of FIG. 22. Thus, the evaluation index data is generated.

Figure 23:
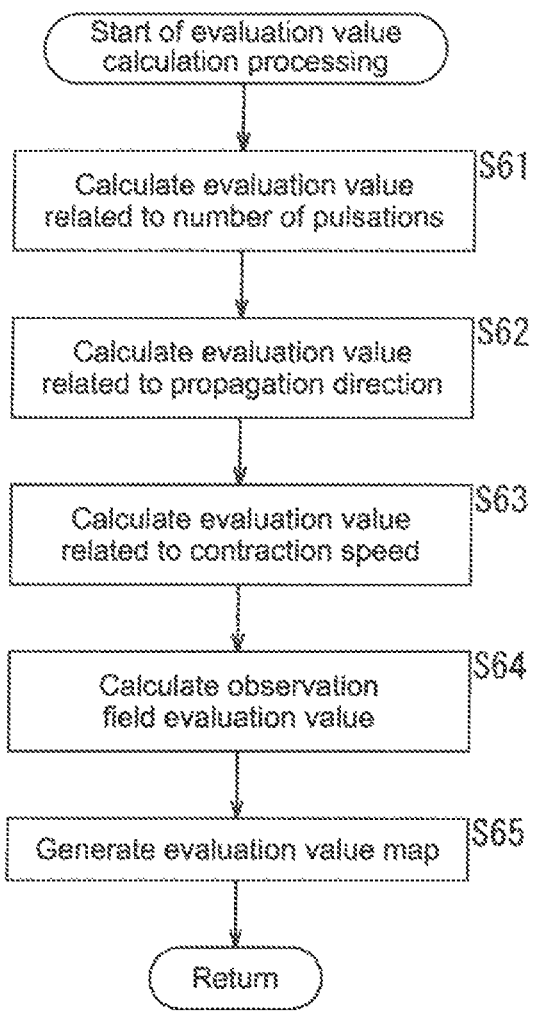
FIG. 23 is a flowchart for describing an example of evaluation value calculation processing.

In Step S23, the evaluation section 104 executes evaluation value calculation processing, which will be described later, with reference to a flowchart of FIG. 23. Thus, the evaluation value is calculated and the evaluation value map described above is generated.

In Step S24, the display section 105 displays information on an observation field. Thus, for example, a screen as described with reference to FIG. 18 is displayed.

In Step S25, the control section 106 determines whether the next observation field is present or not. When it is determined in Step S25 that the next observation field is present, the processing proceeds to Step S26.

In Step S26, the control section 106 moves the stage 107. After that, the processing returns back to Step S21, and the subsequent processing is repeatedly executed. As configured in such a manner, the pulsation information and the evaluation value for each of the observation fields are calculated.

On the other hand, when it is determined in Step S25 that the next observation field is not present, the processing proceeds to Step S27.

In Step S27, the control section 106 determines an observation field. At that time, for example, the observation field is determined on the basis of the evaluation value map.

In such a manner, the observation field determination processing is executed.

Next, the detailed example of the evaluation index data generation processing of Step S22 of FIG. 21 will be described with reference to the flowchart of FIG. 22.

Figure 21:
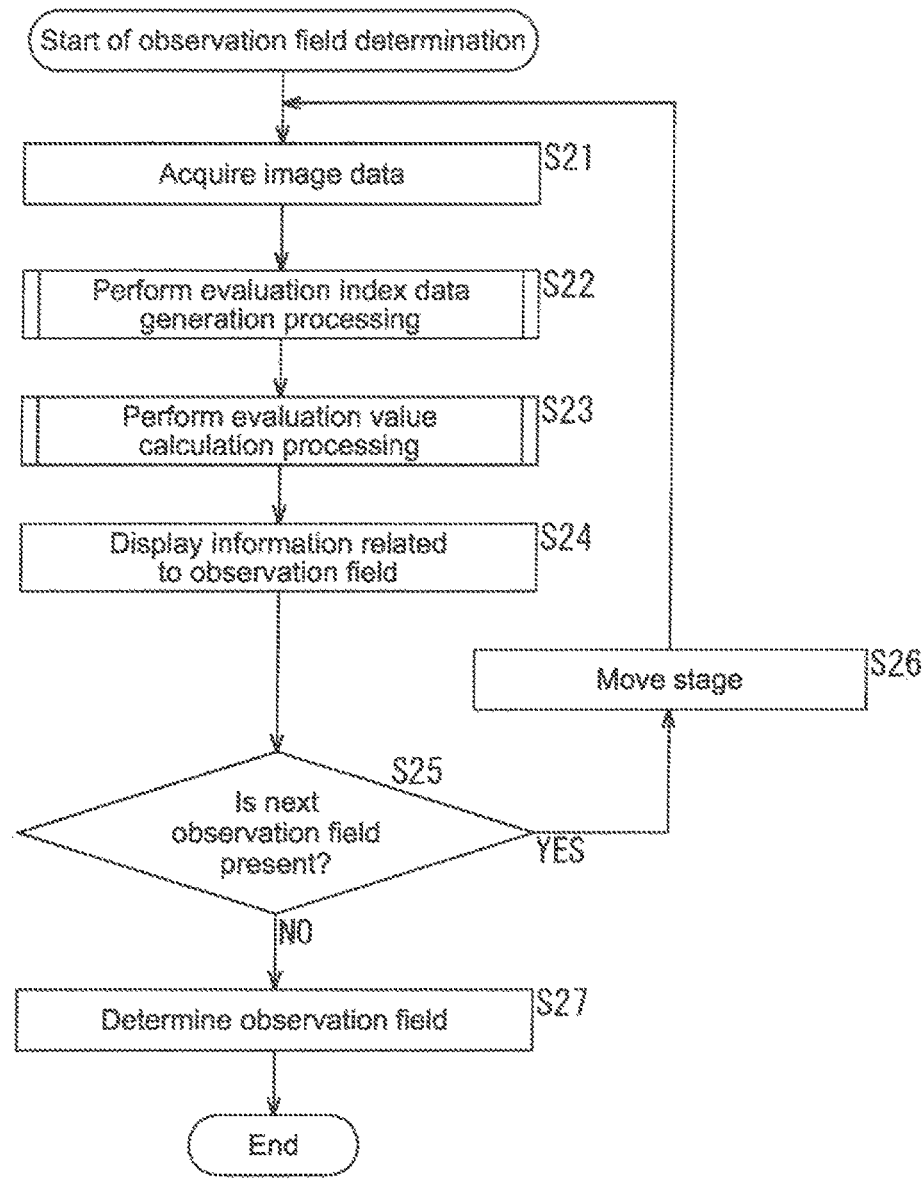
FIG. 21 is a flowchart for describing an example of field determination processing.

In Step S41, the motion detecting section 121 performs motion detection on the basis of the image data obtained in Step S21 of FIG. 21. Thus, as described above, the motion detection data 151 containing the (M×N) pieces of block unit motion detection data 181 is obtained.

In Step S42, the motion amount calculating section 122 calculates a motion amount on the basis of the motion detection data 151 obtained along with the processing of Step S41. At that time, for example, in the motion detection data 151, each piece of frame unit motion detection data 171 each including the (M×N) blocks is divided into the (K×L) blocks 191. An average value of the pieces of block unit motion detection data 181 contained in each of the (K×L) blocks 191 is then calculated, and thus an average motion amount within each block is calculated.

Thus, for example, as shown in FIG. 8, the motion amount data 200 constituted by the T pieces of frame unit motion amount data 201-1 to 201-T is generated.

In Step S43, the pulsation information calculating section 123 calculates the pulsation information. At that time, for example, a pulsation area within an observation field, the number of pulsations within the observation field, a contraction time and a relaxation time of pulsations within the observation field, a contraction speed and a relaxation speed of pulsations, a pulsation duration time, a correlation coefficient, a propagation speed and propagation direction of pulsations, and the like are calculated as the pulsation information.

In Step S44, the pulsation information calculating section 123 outputs the evaluation index data containing the pulsation information calculated in the processing of Step S43.

In such a manner, the evaluation index data generation processing is executed.

Next, an example of the evaluation value calculation processing of Step S23 of FIG. 21 will be described with reference to the flowchart of FIG. 23.

In Step S61, the evaluation section 104 calculates the evaluation value related to the number of pulsations. At that time, for example, the evaluation value E1 is calculated, which evaluates that the number of pulsations within a unit time within an appropriate observation field falls within a certain range.

In Step S62, the evaluation section 104 calculates the evaluation value related to the propagation direction. At that time, for example, the evaluation value E2 is calculated, which represents the smallness (degree of dispersion) of a dispersion value of an average value of the propagation direction related to the plurality of pulsations within that observation field.

In Step S63, the evaluation value related to the contraction speed is calculated. At that time, for example, the evaluation value E3 is calculated, which represents the magnitude of a contraction speed of the pulsations within the observation field.

In Step S64, the evaluation section 104 calculates the observation field evaluation value.

In Step S65, the evaluation section 104 generates the evaluation value map,

In such a manner, the evaluation value calculation processing is executed.

It should be noted that a series of processing described above can be executed by hardware or software. When the series of processing described above is executed by software, programs forming the software are installed from a network or a recording medium in a computer incorporated in dedicated hardware, in a general-purpose personal computer 700 as shown in, for example, FIG. 24, and the like, the general-purpose personal computer 700 being capable of executing various functions by installing various programs therein.

Figure 24:
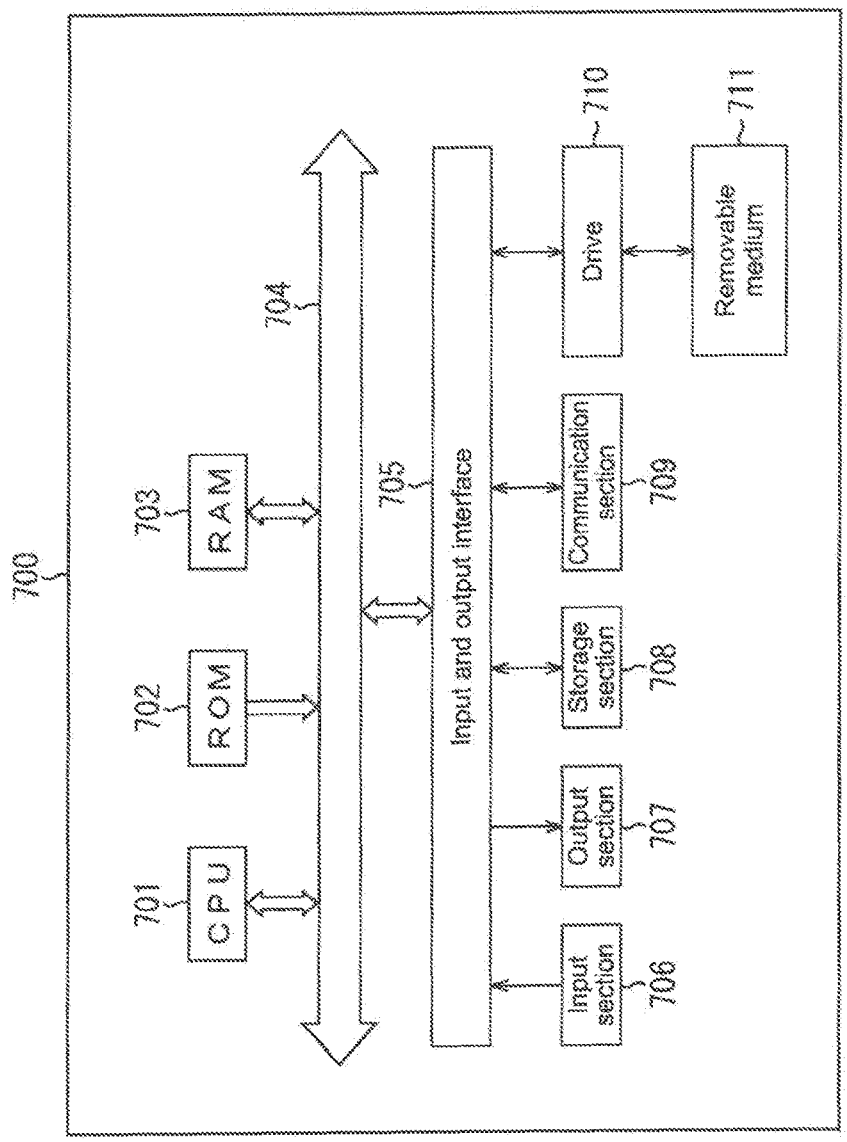
FIG. 24 is a block diagram showing a configuration example of a personal computer.

In FIG. 24, a CPU (Central Processing Unit) 701 executes various types of processing according to a program stored in a ROM (Read Only Memory) 702 and a program that is loaded from a storage section 708 to a RAM (Random Access Memory) 703. The RAM 703 appropriately stores data required for the CPU 701 to execute various types of processing, and the like.

The CPU 701, the ROM 702, and the RAM 703 are connected to one another via a bus 704. An input and output interface 705 is also connected to the bus 704.

The input and output interface 705 is connected with an input section 706 constituted by a keyboard, a mouse, and the like, an output section 707 constituted by a display such as an LCD (Liquid Crystal display), a speaker, and the like, the storage section 708 constituted by a hard disk and the like, and a communication section 709 constituted by a modem, a network interface card such as a LAN card, and the like. The communication section 709 performs communication processing via a network including the Internet.

The input and output interface 705 is also connected with a drive 710 as necessary, to which a removable medium 711 such as a magnetic disc, an optical disc, a magneto-optical disc, or a semiconductor memory is appropriately mounted. A computer program that is read from the removable medium 711 is installed in the storage section 708 as necessary.

When the series of processing described above is executed by software, programs constituting the software are installed from a network such as the Internet or a recording medium constituted by the removable medium 711 and the like.

It should be noted that this recording medium is not limited to a recording medium constituted by the removable medium 711 as shown in FIG. 24, which is provided separate from a main body of the apparatus and distributed so as to deliver programs to a user. The removable medium 711 includes a magnetic disc (including a floppy disk (registered trademark)), an optical disc (including a CD-ROM (Compact Disk-Read Only Memory) and a DVD (Digital Versatile Disk)), a magneto-optical disc (including an MD (Mini-Disk) (registered trademark)), or a semiconductor memory, which stores a program. The recording medium may also include a recording medium constituted by the ROM 702 or a hard disk included in the storage section 708, which stores a program distributed to a user in a state of being built in the main body of the apparatus.

In this specification, the series of processing described above include, in addition to processing that are performed in time series along the described order, processing that are executed in parallel or individually though not processed chronologically.

Further, the embodiment of the present technology is not limited to the embodiment described above and can be variously modified without departing from the gist of the present technology.

It should be noted that the present technology can also have the following configurations.

(1) A cell evaluation apparatus, including:
a motion detecting section configured to detect motion of cultured cardiomyocytes for each of partial areas of a plurality of observation fields on the cultured cardiomyocytes;
a motion amount calculating section configured to calculate a motion amount of the detected motion;
a pulsation information calculating section configured to calculate pulsation information on a characteristic amount of pulsations of the cultured cardiomyocytes on the basis of the calculated motion amount;
an evaluation value calculating section configured to calculate an evaluation value corresponding to the plurality of observation fields, calculated on the basis of the pulsation information; and
a field determining section configured to determine an observation field to be observed on the cultured cardiomyocytes, on the basis of the evaluation value.

(2) The cell evaluation apparatus according to (1), in which
the pulsation information is a pulsation area of the cultured cardiomyocytes within the observation field.

(3) The cell evaluation apparatus according to (1), in which
the motion detecting section detects the motion for each of the partial areas in each of frames of a moving image of the observation area, and
the pulsation information calculating section generates, on the basis of the motion amount for each of the partial areas of the plurality of frames of the moving image, wave shape information representing the pulsations of the cultured cardiomyocytes of each of the partial areas.

(4) The cell evaluation apparatus according to (3), in which the pulsation information is a number of pulsations of the cultured cardiomyocytes within the observation field within a unit time, calculated on the basis of the wave shape information.

(5) The cell evaluation apparatus according to (3), in which the pulsation information is a contraction time or a relaxation time of the pulsations of the cultured cardiomyocytes within the observation field, calculated on the basis of the wave shape information.

(6) The cell evaluation apparatus according to (3), in which the pulsation information is a contraction speed or a relaxation speed of the pulsations of the cultured cardiomyocytes within the observation field, calculated on the basis of the wave shape information.

(7) The cell evaluation apparatus according to (3), in which the pulsation information is a correlation coefficient of a wave shape of the pulsations between the partial areas of the cultured cardiomyocytes within the observation field, calculated on the basis of the wave shape information.

(8) The cell evaluation apparatus according to (3), in which the pulsation information is a propagation speed and a propagation direction of the pulsations of the cultured cardiomyocytes within the observation field, calculated on the basis of the wave shape information.

(9) The cell evaluation apparatus according to any one of (1) to (8), in which the evaluation section calculates the evaluation value that corresponds to each of the plurality of observation fields, before and after predetermined processing performed on the cultured cardiomyocytes, and the observation field determining section determines the observation field by selecting a predetermined number of observation fields from the plurality of observation fields on the basis of a difference between the evaluation values before and after the predetermined processing performed on the cultured cardiomyocytes.

(10) A cell evaluation method, including:

detecting, by a motion detecting section, motion of cultured cardiomyocytes for each of partial areas of a plurality of observation fields on the cultured cardiomyocytes;

calculating, by a motion amount calculating section, a motion amount of the detected motion;

calculating, by a pulsation information calculating section, pulsation information on a characteristic amount of pulsations of the cultured cardiomyocytes on the basis of the calculated motion amount;

calculating, by an evaluation value calculating section, an evaluation value corresponding to the plurality of observation fields, calculated on the basis of the pulsation information; and determining, by a field determining section, an observation field to be observed on the cultured cardiomyocytes, on the basis of the evaluation value.

(11) A program causing a computer to function as a cell evaluation apparatus including:

a motion detecting section configured to detect motion of cultured cardiomyocytes for each of partial areas of a plurality of observation fields on the cultured cardiomyocytes;

a motion amount calculating section configured to calculate a motion amount of the detected motion;

a pulsation information calculating section configured to calculate pulsation information on a characteristic amount of pulsations of the cultured cardiomyocytes on the basis of the calculated motion amount;

an evaluation value calculating section configured to calculate an evaluation value corresponding to the plurality of observation fields, calculated on the basis of the pulsation information; and a field determining section configured to determine an observation field to be observed on the cultured cardiomyocytes, on the basis of the evaluation value.

DESCRIPTION OF REFERENCE SYMBOLS 101 imaging section
102 evaluation target image data generating and recording section
103 evaluation index data generating section
104 evaluation section
105 display section
106 control section
107 stage
121 motion detecting section
122 motion amount calculating section
123 pulsation information calculating section

The invention claimed is:

1. A cell evaluation apparatus, comprising:
circuitry configured to:
  detect motion of cultured cardiomyocytes for each observation field of a plurality of observation fields that correspond to a plurality of partial areas on the cultured cardiomyocytes;
  calculate a motion amount of the detected motion;
  calculate pulsation information on a characteristic amount of pulsations of the cultured cardiomyocytes based on the calculated motion amount,
  wherein the pulsation information, is a pulsation area of the cultured cardiomyocytes within an observation field of the plurality of observation fields, calculated based on comparison of an added value of pieces of block unit motion amount data corresponding to respective blocks with a threshold value,
  wherein each respective block of the respective blocks correspond to a respective area of the plurality of partial areas on the cultured cardiomyocytes;
  calculate an evaluation value corresponding to the plurality of observation fields based on the pulsation information; and
  determine the observation field observed on the cultured cardiomyocytes based on the evaluation value.

2. The cell evaluation apparatus according to claim 1, wherein the circuitry is further configured to:
detect the motion for each observation field of the plurality of observation fields corresponding to the plurality of partial areas in each frame of a plurality of frames of a moving image of an observation area, and
generate, wave shape information that represents the pulsations of the cultured cardiomyocytes of each partial area of the plurality of partial areas based on the motion amount for each observation field of the plurality of observation fields of the plurality of frames of the moving image.

3. The cell evaluation apparatus according to claim 2, wherein the pulsation information is a number of pulsations of the cultured cardiomyocytes within the observation field within a unit time, and wherein the pulsation information is calculated based on the wave shape information.

4. The cell evaluation apparatus according to claim 2, wherein the pulsation information is one of a contraction time or a relaxation time of the pulsations of the cultured cardiomyocytes within the observation field, and wherein the pulsation information is calculated based on the wave shape information.

5. The cell evaluation apparatus according to claim 2, wherein the pulsation information is one of a contraction speed or a relaxation speed of the pulsations of the cultured cardiomyocytes within the observation field, and wherein the pulsation information is calculated based on the wave shape information.

6. The cell evaluation apparatus according to claim 2, wherein the pulsation information is a correlation coefficient of a wave shape of the pulsations between the plurality of partial areas of the cultured cardiomyocytes within the observation field, and wherein the pulsation information is calculated based on the wave shape information.

7. The cell evaluation apparatus according to claim 2, wherein the pulsation information is a propagation speed and a propagation direction of the pulsations of the cultured cardiomyocytes within the observation field, and wherein the pulsation information is calculated based on the wave shape information.

8. The cell evaluation apparatus according to claim 1, wherein the circuitry is further configured to:
calculate the evaluation value that corresponds to each observation field of the plurality of observation fields, before medication and after the medication on the cultured cardiomyocytes, and
determine the observation field based on selection of a subset of observation fields from the plurality of observation fields based on a difference between the evaluation value before the medication and the evaluation value after the medication on the cultured cardiomyocytes.

9. A cell evaluation method, comprising:
in a cell evaluation apparatus comprising circuitry:
detecting, by the circuitry, motion of cultured cardiomyocytes for each observation field of a plurality of observation fields that correspond to a plurality of partial areas on the cultured cardiomyocytes;
calculating, by the circuitry, a motion amount of the detected motion;
calculating, by the circuitry, pulsation information on a characteristic amount of pulsations of the cultured cardiomyocytes based on the calculated motion amount,
wherein the pulsation information, is a pulsation area of the cultured cardiomyocytes within an observation field of the plurality of observation fields, calculated based on comparison of an added value of pieces of block unit motion amount data corresponding to respective blocks with a threshold value,
wherein each respective block of the respective blocks correspond to a respective area of the plurality of partial areas on the cultured cardiomyocytes;
calculating, by the circuitry, an evaluation value corresponding to the plurality of observation fields based on the pulsation information; and
determining, by the circuitry, the observation field observed on the cultured cardiomyocytes based on the evaluation value.

10. A non-transitory computer-readable medium having stored thereon, computer-executable instructions for causing a cell evaluation apparatus to execute operations, the operations comprising:
detecting motion of cultured cardiomyocytes for each observation field of a plurality of observation fields that correspond to a plurality of partial areas on the cultured cardiomyocytes;
calculating a motion amount of the detected motion;
calculating pulsation information on a characteristic amount of pulsations of the cultured cardiomyocytes based on the calculated motion amount,
wherein the pulsation information, is a pulsation area of the cultured cardiomyocytes within an observation field of the plurality of observation fields, calculated based on comparison of an added value of pieces of block unit motion amount data corresponding to respective blocks with a threshold value,
wherein each respective block of the respective blocks correspond to a respective area of the plurality of partial areas on the cultured cardiomyocytes;
calculating an evaluation value corresponding to the plurality of observation fields based on the pulsation information; and
determining the observation field observed on the cultured cardiomyocytes based on the evaluation value.

* * * * *